United States Patent [19]

Dauth et al.

[11] Patent Number: 5,548,070
[45] Date of Patent: Aug. 20, 1996

[54] ORGANOSILICON COMPOUNDS HAVING TRIAZENE GROUPS

[75] Inventors: Jochen Dauth; Bernward Deubzer, both of Burghausen; Elfriede Mayer, Waldkraiburg; Oskar Nuyken, Munich; Brigitte Voit, Munich; Ralf Kollefrath, Munich, all of Germany

[73] Assignee: Wacker-Chemie GmbH, Munich, Germany

[21] Appl. No.: 276,926

[22] Filed: Jul. 19, 1994

[30] Foreign Application Priority Data

Jul. 22, 1993 [DE] Germany ................ 43 24 685.0
May 26, 1994 [DE] Germany ................ 44 18 392.5

[51] Int. Cl.$^6$ ............................................. C07C 245/00
[52] U.S. Cl. .................................................. 534/550
[58] Field of Search ............................................ 534/550

[56] References Cited

U.S. PATENT DOCUMENTS 4,137,226  1/1979  Brodsky et al. .
5,221,759  6/1993  Haeberle et al. .................. 556/413

FOREIGN PATENT DOCUMENTS 2111643     6/1994  Canada .
0602638     6/1994  European Pat. Off. .
WO91/17753  11/1991  WIPO .

OTHER PUBLICATIONS

"New Thermal Cross–Linkers Based on Triazene" by Aldrich N. K. Lau et al. Macromolecules 1992, 25, 7294–7299.
"Darstellung und Strukturen der Silyltriazene" by N. Wiberg et al., Z. Anorg. Allg. Chem. 562, 91 (1988).
Derwent Abstract AN 72–63513T
Derwent Abstract AN 89–035266.

*Primary Examiner*—Paul F. Shaver
*Attorney, Agent, or Firm*—Martin Connaughton

[57] ABSTRACT

The organosilicon compounds have at least one Si—C-bonded organic radical which contains at least one triazene group. The organosilicon compounds can be employed as heat- and light-unstable free radical initiators for the preparation of homo-, graft co- and block copolymers from olefinically unsaturated compounds and for crosslinking organosilicon compounds and organic compounds which can be polymerized by free radical polymerization.

13 Claims, No Drawings

ORGANOSILICON COMPOUNDS HAVING TRIAZENE GROUPS

FIELD OF THE INVENTION

The present invention relates to organosilicon compounds which have Si—C-bonded organic radicals which contain at least one triazene group, processes for the preparation of these compounds, processes for the preparation of homopolymers, graft copolymers and block copolymers from the organosilicon compounds and organic compounds which can be polymerized by free radical polymerization, and a process for crosslinking organosilicon compounds, or organic polymers.

BACKGROUND OF INVENTION

The use of monomeric triazene compounds having organic radicals as heat- and/or photosensitive free radical initiators for free radical polymerization is described in U.S. Pat. No. 4,137,226. Furthermore, the use of bistriazenes as crosslinking agents for fluorine-containing polyimides and aromatic polymers is described in A. Lau, L. Vo, Macromolecules 25, 7294 (1992).

It is advantageous if free radical initiators for silane and organosiloxane compositions are physically compatible with these compositions i.e. miscible or can be dissolved therein. Silyltriazenes which indeed have organosilicon groups but are very unstable and in some cases explosive and therefore not suitable as initiators for industrial applications are known from N. Wiberg et al., Z. Anorg. Allg. Chem. 562, 91 (1988). They are furthermore distinguished by a covalent Si—N bond.

The object of the present invention was to provide silanes and organosiloxanes which can be employed as heat- and/or photosensitive free radical initiators.

SUMMARY OF INVENTION

The present invention relates to organosilicon compounds which have at least one Si—C-bonded organic radical which contains at least one triazene group.

The triazene group

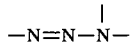

has three open valencies which can be bonded as desired in the organic radicals in the organosilicon compounds according to the invention. The triazene group is bonded to the organosilicon compound via at least one divalent organic radical such that at least one carbon atom is present between the silicon atom and nitrogen atom. Any valences present on the triazene groups and not bonded to the organosilicon compound via a divalent organic radical contain hydroxyl groups or, preferably, N—C— or N—O—C- bonded monovalent organic radicals. The other radicals on the silicon atoms of the organosilicon compounds which contain no triazene groups are preferably hydrogen atoms, halogen atoms or Si—C—, Si—O— or Si—Si-bonded.

Organosilicon compounds are also to be understood as meaning, carbosilanes, silazanes and disilanes, in addition to silanes and siloxanes.

Examples of the monovalent and divalent organic radicals are listed below as radicals $R^1$ and R.

Preferred organosilicon compounds of the invention are organosilicon compounds which are built up from at least one unit containing a triazene group, of the formula

in which

X is a radical of the formula

a radical $R^2$ or half a divalent radical $R^3$, with the proviso that at least one X per unit of formula 1 is a radical of formula 2, and optionally, units of the formula

wherein, in formulae 1 to 3 above,

R is a divalent Si—C-bonded $C_1$- to $C_{18}$-hydrocarbon radical which is optionally substituted by hydroxyl, $C_1$- to $C_6$-alkoxy, mercapto, epoxide or cyano groups or halogen atoms and can contain ether, thioether, amine, ester, carbonyl, urethane, urea, sulfonyl or amide bonds, $R^1$ and $R^2$ are a hydrogen atom, a hydroxyl group, a halogen group or a monovalent $C_1$- to $C_{18}$-hydrocarbon or -hydrocarbonoxy radical which is substituted by hydroxyl, $C_1$- to $C_6$-alkoxy, mercapto, epoxide or cyano groups or halogen atoms and can contain ether, thioether, amine, ester, carbonyl, urethane, urea, sulfonyl or amide bonds, $R^3$ is a divalent $C_1$- to $C_{18}$-hydrocarbon radical which is substituted by hydroxyl, $C_1$- to $C_6$-alkoxy, mercapto, epoxide or cyano groups or halogen atoms and can contain ether, thioether, amine, ester, carbonyl, urethane, urea, sulfonyl or amide bonds and m and n represents 0, 1, 2 or 3.

If X in formula 1 is half a radical $R^3$, two units of formula 1 are thereby bonded via $R^3$.

If two radicals X in formula 1 are each half a radical $R^3$, cyclization to give the triazene can take place.

Examples of unsubstituted hydrocarbon radicals $R^1$ and $R^2$ are alkyl radicals, such as the methyl, ethyl, n-propyl, iso-propyl, n-butyl, iso-butyl, tert-butyl, n-pentyl, iso-pentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; alkenyl radicals, such as the vinyl, allyl, n-5-hexenyl, 4-vinylcyclohexyl and the 3-norbornenyl radical; cycloalkyl radicals, such as cyclopentyl, cyclohexy, 4-ethylcyclohexyl and cycloheptyl radicals, norbornyl radicals and methylcyclohexyl radicals; aryl radicals, such as the phenyl, biphenylyl, naphthyl, anthryl and phenanthryl radical; alkaryl radicals, such as o-, m- and p-tolyl radicals, xylyl radicals and ethylphenyl radicals; aralkyl radicals, such as the benzyl radical and the α-phenyl- and the β-phenylethyl radical, and the corresponding hydrocarbonoxy radicals.

Examples of substituted hydrocarbon radicals as the radicals $R^1$ and $R^2$ are halogenated hydrocarbon radicals, such as the chloromethyl, 3-chloropropyl, 3-bromopropyl, 3,3,3-trifluoropropyl and 5,5,5,4,4,3,3-heptafluoropentyl radical and the chlorophenyl, dichlorophenyl and trifluorotolyl radical; mercaptoalkyl radicals, such as the 2-mercaptoethyl and 3-mercaptopropyl radical; cyanoalkyl radicals, such as the 2-cyanoethyl and 3-cyanopropyl radical; aminoalkyl radicals, such as the 3-aminopropyl, N-(2-aminoethyl)-3-aminopropyl and N-(2-aminoethyl)-3-amino( 2-methyl)propyl radical; aminoaryl radicals, such as the aminophenyl radical; acyloxyalkyl radicals, such as the 3-acryloyloxypropyl and 3-methacryloyloxypropyl radical; hydroxyalkyl radicals, such as the hydroxypropyl radical, and radicals of the formulae

and $HOCH_2CH(OH)CH_2SCH_2CH_2-$, and the corresponding hydrocarbonoxy radicals.

Other examples for $R^1$ and $R^2$, in particular for $R^2$, are substituted aromatic hydrocarbon radicals, such as the nitrophenyl, cyanophenyl, methoxyphenyl, ethoxyphenyl, hydroxyphenyl, dimethoxyphenyl, halophenyl, n-butylphenyl, mercaptophenyl, carboxyphenyl, diethylaminophenyl, acetaminophenyl, tolyl and azobenzyl radical, and heteroaromatic radicals, such as the pyridinyl, furyl, imidazolyl and thiophenyl radical.

The radical $R^1$ is particularly preferably a hydrogen atom or the methyl, ethyl, n-propyl, vinyl, 3-norbornenyl, n-5-hexenyl, tolyl, phenyl, methoxy, ethoxy, i-propoxy or n-propoxy radical, and in particular the methyl radical.

The radical $R^2$ is particularly preferably a hydrogen atom or a methyl, n-butyl, n-cyclohexyl, phenyl, methoxyphenyl, n-butylphenyl, dimethoxyphenyl, tolyl, diethylaminophenyl, halophenyl, hydroxyphenyl or cyanophenyl radical.

Examples of divalent hydrocarbon radicals R and $R^3$ are saturated, branched or unbranched alkylene radicals, such as the methylene and ethylene radical, and n-propylene, butylene, pentylene, 1-methylpentylene, hexylene, cyclohexylene and octadecylene radicals, or unsaturated alkylene or arylene radicals, such as the hexenylene radical, phenylene radicals, such as the 2-chloro-1,4-phenylene radical, or radicals such as $C_6H_4CH_2C_6H_4$, $C_6H_4C_6H_4$ or $C_6H_4C(CH_3)_2C_6H_4$.

Examples of substituents on the divalent hydrocarbon radicals R and $R^3$ are halogen atoms and $C_1$-$C_6$-alkoxy radicals. Other examples of substituted radicals R and $R^3$ are $-C_2F_4-$, $C_3H_6NHC_2H_4-$, $C_3H_6OC_2H_4-$, $C_6H_4OC_6H_4-$, $C_6H_4SO_2C_6H_4-$, $C_6H_4SC_6H_4-$, $C_6H_4NHC_6H_4-$, $C_7H_6O-$, $C_6H_3Cl-$, $C_{12}H_8N_2-$, $C_7H_6S-$ and $C_6H_4COC_6H_4-$.

The radicals R and $R^3$ are preferably $C_1$-$C_6$-alkylene radicals, which are not substituted. n-Propylene radicals are more preferred.

Preferred units or combinations of two units of formula 1 containing triazene groups have the formulae $$Y-N=N-NR^2-Y \quad (4)$$

$$Y-N=N-N(Y)_2 \quad (5)$$

$$Y-N=N-N(R^2)_2 \quad (6)$$

$$Y-N=N-NR^2-R^3-NR^2-N=N-Y \quad (7)$$

$$Y-NR^2-N=N-R^3-N=N-NR^2-Y \quad (8)$$

$$(Y)_2N-N=N-R^3-N=N-N(Y)_2 \quad (9)$$

$$(Y)_2N-N=NR^2 \quad (10)$$

$$Y-NR^2-N=NR^2 \quad (11)$$

$$Y-N=N-N(Y)-R-N(Y)-N=N-Y \quad (12)$$

wherein

Y is a radical of formula 2 and

R, $R^2$ and $R^3$ have the above meanings.

Preferred units containing triazene groups have the formulae 8 and 11, in particular 11.

If the organosilicon compounds have units of formula 3, the organosilicon compounds contain siloxane constituents which can be linear, cyclic, branched, elastomeric or crosslinked in a resin-like manner in order to be miscible or compatible with corresponding siloxane compositions or other compositions.

The organosilicon compounds can be in solid or liquid form. They can have any desired structures known for organosilicon compounds. For example, the organosilicon content can be interrupted by triazene units, or the triazene units may be bonded as side groups in the organosilicon compounds. The organosilicon content can be linear, branched or crosslinked in a resin-like manner.

If the organosilicon compound has no units of formula 3, silanes exist. If the organosilicon compound has units of formula 3, siloxanes exist.

Preferred examples of organosilicon compounds are linear diorganopolysiloxanes which contain exclusively hydrogen, methyl, phenyl or 3,3,3-trifluoropropyl radicals as radicals $R^1$ in the chain in the units of formula 3, and triazene units of formula 1 as side groups.

The content of units of formula 3 in the organosilicon compounds can be very high if the organosilicon compounds are employed as a grafting base for copolymers. For example, up to 1000, perferably 5–50, units of formula 3 can be present per unit of formula 1.

The invention also relates to processes for the preparation of organosilicon compounds which have at least one Si—C-bonded organic radical which contains at least one triazene group.

Process 1

In this process, diazonium salts are reacted with primary or secondary amines, at least one of the radicals on the diazonium salts or amines having a Si—C-bonded organosilicon radical.

A process for the preparation of organosilicon compounds which are built up from at least one unit of formula 1 containing a triazene group, in which the diazonium salts of the formula $$X-N=N^\oplus Z^\ominus \quad (13)$$

are reacted with amines of the formula $$\begin{array}{c} H-N-X, \\ | \\ X \end{array} \quad (14)$$

wherein

X has the meanings given above in formula 2 and

Z is preferably a known anionic radical,

Process 1 is preferably carried out in water, alcohols, such as methanol, ethanol or isopropanol, or in the organic solvents mentioned below for process 3.

Preferred examples of anions Z are Cl, Br, F, $PF_6$, $BF_4$, $SbF_6$, $CH_3C_6H_4SO_3$, $CH_3COO$, $CF_3COO$ and $CF_3SO_3$.

Process 2

In this process, (A) triazene compounds which carry radicals which have epoxide or carboxylic acid anhydride groups, halogen atoms or —COCl or —NCO groups are reacted with organosilicon compounds containing —OH, —NHR$^1$, COOH or —SH groups, or (B) triazene compounds which carry radicals which have groups such as —COOH, —OH, —NHR$^1$ or —SH are reacted with organosilicon compounds which have epoxide or carboxylic acid anhydride groups, halogen atoms or —COCl or —NCO groups. R$^1$ has the above meanings.

A process (A) for the preparation of organosilicon compounds which are built up from at least one unit of formula 1 containing a triazene group, wherein compounds of the formula $$B-N=N-N(B)-B, \quad (15)$$

in which

B is a monovalent $C_1$- to $C_{17}$- hydrocarbon radical which has a carboxylic acid anhydride or epoxide group or a —COCl or —NCO group, is optionally substituted by hydroxyl, $C_1$- to $C_6$-alkoxy, mercapto, epoxide or cyano groups or halogen atoms and can contain ether, thioether, amine, ester, carbonyl, urethane, urea, sulfonyl or amide bonds, a radical of formula 2, a radical R$^2$ or half a divalent radical R$^3$, with the proviso that at least one B per compound of formula 15 is a monovalent radical, described above, which has a carboxylic acid anhydride or epoxide group or a —COCl or —NCO group, are reacted with compounds of the formula $$A-G \quad (16),$$

in which

A is an —OH, —NHR$^1$, —COOH or —SH group,

G is a radical of formula 2 and

R$^2$ and R$^3$ have the above meanings, is preferred.

A corresponding process (B) for the preparation of organosilicon compounds which are built up from at least one unit of formula 1 containing a triazene group, wherein, in formula 15, B can contain —OH, —NHR$^1$, —COOH or —SH groups and in formula 16, A is halogen atoms, carboxylic acid anhydride or epoxide groups or —COCl or —NCO groups, is likewise preferred.

Process 2 is preferably carried out in the organic solvents mentioned below for process 3.

Process 3

In this process, triazene compounds which carry radicals which have olefinic double bonds or acetylenic triple bonds are reacted with organosilicon compounds which have Si—H groups in the presence of platinum, rhodium or compounds thereof.

A process for the preparation of organosilicon compounds which are built up from at least one unit of formula 1 containing a triazene group, wherein compounds of the formula $$Z-N=N-N(Z)-Z, \quad (17)$$

in which

Z is a monovalent $C_1$- to $C_{18}$-hydrocarbon radical which has an olefinic double bond or acetylenic triple bond, is optionally substituted by hydroxyl, $C_1$- to C6-alkoxy, mercapto, epoxide or cyano groups or halogen atoms and can optionally contain ether, thioether, amine, ester, carbonyl, urethane, urea, sulfonyl or amide bonds, a radical of formula 2, a radical R$^2$ or half a divalent radical R$^3$, with the proviso that at least one Z per compound of formula 17 is a monovalent radical described above which has an olefinic double bond or acetylenic triple bond, are reacted with compounds of the formula $$H-SiR^1{}_oO_{\frac{3-o}{2}}, \quad (18)$$

in which o is 0, 1, 2 or 3 and

R$^1$ and R$^2$ have the above meanings, in the presence of platinum, rhodium or compounds thereof, is preferred.

All the catalysts which have also been employed for addition of hydrogen atoms bonded directly to Si atoms onto aliphatically unsaturated compounds can be employed for the above reaction. Examples of such catalysts are metallic and finely divided platinum, which can be on supports, such as silicon dioxide, aluminium oxide or active charcoal, compounds of complexes of platinum, such as platinum halides, for example $PtCl_4$, $H_2PtCl_6 \cdot 6H_2O$ or $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, in particular platinum-divinyltetramethyldisiloxane complexes with or without a content of detectable inorganically bonded halogen, bis-(gamma-picoline)platinum dichloride, trimethylenedipyridineplatinum dichloride, dicyclopentadieneplatinum dichloride, dimethyl sulfoxide-ethyleneplatinum(II) dichloride and reaction products of platinum tetrachloride with olefin and primary amine or secondary amine or primary and secondary amine, such as the reaction product of platinum tetrachloride, dissolved in 1-octene, with sec-butylamine, or ammonium-platinum complexes.

The catalyst is preferably employed in amounts of 0.5 to 500 ppm by weight (parts by weight per million parts by weight), in particular 2 to 400 ppm by weight, calculated as elemental metal and based on the total weight of the silanes and/or siloxanes present in the reaction mixture which have hydrogen atoms bonded directly to silicon atoms.

The reaction mentioned (called hydrosilylation below) can be carried out in the absence or in the presence of solvents, the presence of solvents being preferred.

If the solvents are used, solvents or solvent mixtures which are largely inert under the reaction conditions, in particular those having a boiling point or boiling range of up to 120° C. under 0.1 MPa, are preferred. Examples of such solvents are ethers, such as dioxane, tetrahydrofuran, diethyl ether and diethylene glycol dimethyl ether; chlorinated hydrocarbons, such as methylene chloride, chloroform, carbon tetrachloride, 1,2-dichloroethane and trichloroethylene; hydrocarbons, such as pentane, n-hexane, hexane isomer mixtures, heptane, octane, wash benzine, petroleum ether, benzene, toluene and xylenes; ketones, such as acetone, methyl ethyl ketone and methyl isobutyl ketone; carbon disulfide and nitrobenzene, dimethylacetamide, dimethylformamide, dimethyl sulfoxide, N-methylpyrrolidone or mixtures of these solvents.

The term solvent does not mean that all the reaction components must dissolve in the solvent. The reaction can also be carried out in a suspension or emulsion of one or more of the reaction partners. The reaction can also be carried out in a solvent mixture having a miscibility gap, at least one reaction partner being soluble in each of the mixed phases.

The hydrosilylation can be carried out under the pressure of the surrounding atmosphere of about 0.1 MPa (absolute), but it can also be carried out under higher or under lower pressures. Pressures of 0.01 MPa to 1.0 MPa are preferred, in particular those from 0.09 MPa to 0.11 mPa.

Process 4

The silanes which contain groups which can undergo condensation can be hydrolyzed, condensed or equilibrated by reaction with silanes or siloxanes containing groups which can undergo condensation to give the organosiloxanes.

In the preferred process for the preparation of organosiloxanes which have at least one unit of formula 1 containing a triazene group and units of formula 3, units of formula 1 containing triazene groups, in which X is a radical of formula 2 in which at least one radical $R^1$ is a halogen, hydroxyl or $C_1$- to $C_6$-alkoxy radical, are reacted with organosilicon compounds from units of the formula

$$SiR^1_pO_{\frac{4-p}{2}}, \qquad (19)$$

in which p is 0, 1, 2, 3 or 4 and $R^1$ has the meanings given in formula 2, with the proviso that in formula 19, at least one radical $R^1$ is a $C_1$- to $C_6$-alkoxy radical, a halogen atom or a hydroxyl group.

The above process is preferably carried out in the presence of a catalyst.

Examples of such catalysts are sulfuric acid, phosphoric acid, trifluoromethanesulfonic acid, iron(II) chloride, aluminum chloride, boron trifluoride, zinc chloride, kaolin, acid zeolites, sulfonated charcoal, alkali metal hydroxides, preferably potassium hydroxide and cesium hydroxide, alkali metal alcoholates, quaternary ammonium hydroxides, such as tetramethyl ammonium hydroxide, benzyltrimethylammonium hydroxide, benzyltriethylammonium hydroxide, benzyltrimethylammonium butylate and β-hydroxyethyltrimethylammonium 2-ethylhexanoate, quaternary phosphonium hydroxides, such as tetra-n-butylphosphonium hydroxide and tri-n-butyl- 3-[tris(trimethylsiloxy)silyl]-n-propyl-phosphonium hydroxide, alkali metal siloxanolates and ammonium organosiloxanolates, such as benzyltrimethylammonium ethylsiloxanolate, and phosphorus-nitrogen compounds, such as phosphoronitrile chloride.

The catalyst is preferably employed in amounts of 0.1% to 10% by weight, based on the sum of units of formula 1 containing triazene groups and organosilicon compounds from units of formula 19.

The above preparation processes 1 to 4 are preferably carried out at temperatures of −10° C. to 150° C., in particular from 0° C. to 100° C. The above preparation processes are preferably carried out with exclusion of light.

Preferably, all the volatile contents and salts are removed after the synthesis in the above preparation processes.

The organosilicon compounds are preferably employed as free radical initiators for homopolymerization, graft copolymerization and block copolymerization of organic compounds which can be polymerized by free radical polymerization.

The invention furthermore relates to a process for the preparation of graft copolymers and block copolymers in which the organosilicon compounds are reacted with organic compounds which can be polymerized by free radical polymerization.

The process for the preparation of homo- and copolymers can be carried out in bulk or in the presence of organic solvents, it being possible for the organosilicon compounds to be partly or completely dissolved. The process is preferably carried out in solution. Solvents which are preferably employed are ethers, such as tetrahydrofuran and dioxane, or hydrocarbons, such as toluene and xylene. Organic solvents are preferably employed in 0 to 20 times the amount by weight, in particular in 1 to 10 times the amout of the organosilicon compounds according to the invention.

The organosilicon compounds are preferably initially introduced into the reaction vessel together with the solvent. However, it is also possible for all the components of the process to be mixed, before the initiator is activated.

The reaction is preferably carried out with exclusion of oxygen. The reaction mixture is preferably saturated with nitrogen for 10 to 90 minutes, and the pH should preferably be 7–9 before the free radical initiator is activated. Preferably, organic compounds which can be polymerized by free radical polymerization are metered into the mixture in an amount which is 1% to 95% by weight, in particular 20% to 80% by weight, based on the total weight of the homo- or copolymer.

Preferably, monomeric olefinically unsaturated organic compounds are employed as organic compounds which can be polymerized by free radical polymerization. Acrylic acid, methacrylic acid, acrylic acid esters or methacrylic acid esters of aliphatic alcohols and diols having 1 to 10 C atoms, acrylonitrile, acrylamide, styrene, p-methylstyrene, vinyl acetate, vinyl propionate, maleimide, vinylpyrrolidone, vinyl chloride, ethylene, butadiene, isoprene and 2-chloro-1,4-butadiene are preferably employed. Styrene, acrylamide, butadiene, isoprene and acrylic acid esters and methacrylic acid esters of aliphatic alcohols having 1 to 4 C atoms, for example methyl (meth)acrylate, ethyl (meth)acrylate or butyl (meth)acrylate and ethylene glycol di(meth)acrylate, are particularly preferred. Both homopolymers and copolymers of the monomers mentioned are suitable as the organic polymer component. Graft polymerization with monomers which contain two ethylenic double bonds leads to crosslinked graft polymers.

Grafting onto the organopolysiloxane free radical macroinitiators is preferably started by increasing the temperature to about 40° to 150° C., preferably 60° to 120° C. The starting temperature is maintained for 30 minutes to 24 hours to bring the polymerization to completion. Grafting can also be carried out by UV irradiation with a mercury or mercury/xenon lamp for up to 24 hours.

The isolation of the homo-, graft co- or block copolymers from the solution and the removal of residual amounts of unreacted organic monomer are carried out by precipitation or by other known purification methods.

The homopolymers, graft copolymers or block copolymers are yellowish oils or solids. The homopolymers, graft copolymers or block copolymers prepared by the process have a defined structure due to controlled bonding of the organopolymer chains to the silicon base.

The invention furthermore relates to the homopolymers, graft copolymers and block copolymers obtainable by the process.

The average molecular weight of the homopolymers, graft copolymers and block copolymers is preferably $10^3$ to $10^7$ g/mol, in particular $5 \times 10^3$ to $5 \times 10^5$ g/mol.

The homopolymers, graft copolymers and block copolymers are suitable above all for use as modified thermoplastics and for use as additives for polymer modification, in particular as agents which impart compatibility to silicon-containing polymer blends or as a silicon constituent in polymers or polymer blends.

The invention further relates to a process for crosslinking organosilicon compounds or organic compounds which can be polymerized by free radical polymerization, in which the organic compounds are mixed with the organic silicon compounds and the mixture is heated or irradiated with UV light.

The organosilicon compounds which serve as free radical initiators are preferably thermolyzed or photolyzed in bulk.

The mixture is preferably heated to about 40° to 200° C., preferably 60° to 170° C.

The organosilicon compounds and organic compounds are crosslinked by generation and/or combination of the free radicals formed. Both monomers and polymers can be crosslinked.

Silicone systems which have olefinic double bonds are preferably crosslinked. There is the possibility of crosslinking polyfunctional unsaturated systems, such as bisacrylates and polybutadiene, with the organosilicon compounds as free radical initiators, in which case blends can also form.

The organosilicon compounds can also be used as a blowing agent and dye. In the following examples, unless stated otherwise,
(a) all data amounts are based on the weight;
(b) all pressures are 0.10 mPa (absolute);
(c) all temperatures are 20° C.

The following abbreviations have been used:
of th.=of therory
p.a.=analytical grade
THF=tetrahydrofuran
GPC=gel permeation chromatography

EXAMPLES

General preparation of the diazonium salts in an aqueous system 0.25 mol of the corresponding aniline derivative was dissolved in 200 ml of 10% strength aqueous hydrochloric acid, and the mixture was then stirred with 1 g of active charcoal for 5 minutes and filtered. A solution of 17.25 g (0.25 mol) of sodium nitrite in 30 g of water was added to the filtrate at 0° C., with exclusion of light. After 1 hour, 54.55 g (0.5 mol) of sodium tetrafluoroborate were added at 0° C. and the resulting suspension was stirred for 30 minutes. In the case of bisaniline derivatives, twice the amount of aqueous hydrochloric acid, sodium nitrite, sodium terafluoroborate and water were employed.

The products were filtered off, rinsed three times with ice-water and then dried to constant weight under a high vacuum. The diazonium salts were obtained as white to pale yellow solids with yields of between 60% and 80% of theory.

The diazonium salts were then employed for the triazene syntheses without further storage.

All the operations were carried out with absolute exclusion of light.

EXAMPLE 1

Synthesis of free radical macroinitiator RM 1

40 g ($2.6 \times 10^{-2}$ mol of NHR function, R=cyclohexyl, viscosity=836 mm$^2$/s) of a polydimethylsiloxane functionalized with N-cyclohexylaminopropyl side groups were dissolved in 70 ml of absolute THF and 2.69 g ($2.6 \times 10^{-2}$ mol) of triethylamine and the solution was cooled to 0° C. A total of 6.6 g ($3 \times 10^{-2}$ mol) of 4-methoxybenzenediazonium tetrafluoroborate were added slowly and in portions. The solution was stirred at 0° C. for an additonal hour. Solid constituents were filtered off. After addition of 50 ml of diethyl ether, the mixture was washed with 2×100 ml of water, the organic phase was dried over magnesium sulfate and the solvent was removed in vacuo. The oily, red product was dried to constant weight under a high vacuum.

Yield: 35 g (76% of th.)

EXAMPLE 2

Synthesis of free radical macroinitiator RM 2

30 g ($7.6 \times 10^{-3}$ mol of NHR function, R=cyclohexyl, viscosity=816 mm$^2$/s) of a polydimethylsiloxane functionalized with N-cyclohexylaminopropyl groups were dissolved in 60 ml of absolute THF and 0.77 g ($7.6 \times 10^{-3}$ mol) of triethylamine and the solution was cooled to 0° C. A total of 1.7 g ($7.6 \times 10^{-3}$ mol) of 4-methoxybenzenediazonium tetrafluoroborate were added slowly and in portions. The solution was stirred at 0° C. for an additional hour. Solid constituents were filtered off. After addition of 50 ml of diethyl ether, the mixture was washed with 2×100 ml of water, the organic phase was dried over magnesium sulfate and the solvent was removed in vacuo. The oily, red product was dried to constant weight under a high vacuum.

Yield: 26 g (83% of th.)

EXAMPLE 3

Synthesis of free radical macroinitiator RM 3

30 g ($5.3 \times 10^{-2}$ mol of NHR function, R=cyclohexyl, viscosity=826 mm$^2$/s) of a polydimethylsiloxane functionalized with N-cyclohexylaminopropyl groups were dissolved in 60 ml of absolute THF and 5.42 g ($5.3 \times 10^{-2}$ mol) of triethylamine and the solution was cooled to 0° C. A total of 11.7 g ($5.3 \times 10^{-2}$ mol) of 4-methoxybenzenediazonium tetrafluoroborate are added slowly and in portions. The solution was stirred at 0° C. for an additional hour. Solid constituents were filtered off. After addition of 50 ml of diethyl ether, the mixture was washed with 2×100 ml of water, the organic phase was dried over magnesium sulfate and the solvent was removed in vacuo. The oily, red product was dried to constant weight under a high vacuum.

Yield: 33 g (80% of th.)

EXAMPLE 4

Synthesis of free radical macroinitiator RM 4

16.4 g ($9.7 \times 10^{-3}$ mol of NHR function, R=cyclohexyl, viscosity=738 mm$^2$/s) of a polydimethylsiloxane functionalized with N-cyclohexylaminopropyl groups were dissolved in 50 ml of isopropanol. A total of 7.3 g ($3.8 \times 10^{-2}$ mol) of benzenediazonium tetrafluoroborate were added slowly and in portions. The solution was buffered into the slightly alkaline range (pH=8) with sodium bicarbonate and was stirred at 40° C. for 2 hours. The solvent was then removed at 30° C. under a high vacuum, the residue was taken up in diethyl ether and the mixture was extracted by shaking twice with 25 ml of water in a separating funnel. The ether phase was dried with sodium sulfate and the ether was evaporated. The orange-red, highly viscous oil was dried to constant weight under a high vacuum.

Yield: 13.2 g (75.8% of th.)

EXAMPLE 5

Synthesis of free radical macroinitiator RM 5

44.3 g ($1.95 \times 10^{-2}$ mol of NH$_2$ function, viscosity=836 mm$^2$/s) of a polydimethylsiloxane functionalized with aminopropyl groups were dissolved in 150 ml of THF and 7.7 g ($7.6 \times 10^{-2}$ mol %) of triethylamine and the solution was cooled to 0° C. A total of 4.23 g ($1.95 \times 10^{-2}$ mol) of 4-cyanobenzenediazonium tetrafluoroborate were added slowly and in portions. The solution was stirred at 0° C. for an additional hour. 100 ml of diethyl ether were then added to the solution in a separating funnel and the mixture was extracted by shaking three times with 100 ml of 0.01 molar aqueous hydrochloric acid. The organic phase was then dried with sodium sulfate and the solvent was evaporated. The red-brown, oily product was dried to constant weight under a high vacuum.

Yield: 36.1 g (77% of th.)

EXAMPLE 6

Synthesis of free radical macroinitiator RM 6

A saturated solution of 0.28 g ($2.6 \times 10^{-3}$ mol) of sodium carbonate in water and a precooled solution of 7.38 g ($1.3 \times 10^{-3}$ mol of NHR function, R=cyclohexyl) of a polydimethylsiloxane of chain length 70 functionalized with α,w-cyclohexylaminopropyl groups in THF was added to a solution, cooled to −10° C., of 0.58 g ($1.3 \times 10^{-3}$ mol) of 4,4'-bisdiazoniumdiphenyl sulfone-tetrafluoroborate in 30 ml of dimethylacetamide, while stirring constantly. When the evolution of gas had subsided, the mixture was stirred at 0° C. for 30 minutes. 200 ml of water and 50 ml of diethyl ether were added to the reaction mixture in a separating funnel. The mixture was washed several times with water, the organic phase was dried over sodium sulfate, the solvent was removed in vacuo and the product was dried to constant weight under a high vacuum. A red, viscous oil was obtained.

Yield: 3.5 g (44% of th.)

EXAMPLE 7

Synthesis of free radical macroinitiator RM 7

500 g of water, 6 g of Dodigen® 226 (Hoechst AG; coconut alkyl-dimethylbenzylammonium chloride, 50% strength in water) and 0.5 g of sodium hyroxide solution (10% strength in water) were initially introduced into the reaction vessel, and a mixture of 95.6 g (0.7 mol) of methyltrimethoxysilane and 4.4 g (0.02 mol) of aminopropyltriethoxysilane was added at 65° C. in the course of three hours, while stirring. After the mixture had been stirred for an additional 2 hours, a stable, clear, slightly opalescent dispersion having a solids content of 7% and a pH of 10 was obtained 50 g ($1.35 \times 10^{-3}$ mol of NH$_2$ function) of the dispersion were initially introduced into the reaction vessel at room temperature, and 0.29 g ($1.35 \times 10^{-3}$ mol) of 4-cyanobenzenediazonium tetrafluoroborate and 0.45 g ($4.4 \times 10^{-3}$ mol) of tri-ethylamine were added. The dispersion was then stirred at room temperature for 2 hours and the orange-yellow solid was filtered off. The product was washed alternately with water and methanol until the filtrate was colorless. Drying of the orange-yellow, fine solid was carried out to constant weight under a high vacuum at room temperature.

Yield: 2.0 g (78% of th.)

EXAMPLE 8

Synthesis of free radical macroinitiator RM 8

1.55 g (0.013 mol) of 3-aminostyrene were dissolved in 30 ml of two-molar aqueous hydrochloric acid, 40 ml of water were added and the mixture was diazotized with 0.897 g (0.013 mol) of sodium nitrite in a little water at 0° C. The diazonium salt solution was added to a solution, cooled to 0° C., of 25 g of sodium acetate and 0.95 g (0.013 mol) of diethylamine in water, while stirring. 50 ml of ether were added to the reaction mixture in a separating funnel and the mixture was washed several times with 50 ml of water. The organic phase was dried over sodium sulfate and concentrated in vacuo. The product was purified over silica gel (mobile phase pentane/ether 3:1).

Yield: 1.05 g (40% of th.)

10.2 g of 3-vinylphenyldiethyltriazene were heated up to 80° C. together with 40 g of a copolymer of trimethylsiloxane, dimethylsiloxane and methylsiloxane units having a viscosity of 238 mm$^2$/s at 25° C., which contained 0.025% by weight of Si-bonded hydrogen, and 12.35 mg of a 1,3-divinyl-1,1,3,3-tetramethyldisiloxane complex of platinum having a platinum content of 17% by weight, while stirring and under an inert gas. A further 160 g of the above mentioned copolymer were then metered in over a period of 1 hour. After a reaction time of 1 hour at a temperature of 80° C., 6.1 mg of the above mentioned platinum catalyst were again added and the mixture was allowed to after-react at 50° C. for an additional hour. The red oil was heated thoroughly at 50° C. under a high vacuum.

Yield: 195 g (93% of th.)

EXAMPLE 9

Synthesis of free radical macroinitiator RM 9

12.3 g (0.05 mol) of N-cyclohexylamino-propyldimethoxymethylsilane and 13 g (0.11 mol) of trimethylethoxysilane were initially introduced into the reaction vessel. A solution of 22 mg ($5.5 \times 10^{-4}$ mol) of sodium hydroxide in 4 ml of water was added dropwise, while stirring constantly. The resulting emulsion was heated at 60° C. for 1 hour, a clear solution forming. All the highly volatile compounds were distilled off under normal pressure at 100° C. The residue was heated under reflux with 6 ml of 20% strength aqueous hydrochloric acid for 4 hours under reflux and the non-aqueous phase was separated off, washed twice with water and distilled under 1 mbar (boiling point 120° C. to 121° C.).

Yield: 5.53 g (31% of th.)

3.68 g ($16.6 \times 10^{-3}$ mol) of p-methoxybenzenediazonium tetrafluoroborate and 1.7 g ($16.6 \times 10^{-3}$ mol) of triethylamine, dissolved in THF, were added dropwise to 3 g ($8.3 \times 10^{-3}$ mol) of the bis[trimethylsiloxy]-N-cyclohexylaminopropyl-methylsilane prepared above, dissolved in 20 ml of THF and cooled to 0° C. The reaction mixture was stirred at 0° C. for 1 hour. Solid constituents were filtered off, 50 ml of diethyl ether were added to the mixture and the mixture was washed twice with 100 ml of water. The organic phase was dried over sodium sulfate and the solvent was stripped off in vacuo. The product was dried under a high vacuum. A red oil was obtained.

Yield: 4 g (60% of th.)

2.4 g (0.005 mol) of the red oil were initially introduced into the reaction vessel with 26 g of a non-blocked polydimethylsiloxane of viscosity 100 mm²/s at room temperature and 0.142 g (0.55 mmol) of tetrabutylammonium hydroxide in 50 ml of toluene. The solution was heated to 80° C. and stirred for 4 hours. The solvent was then evaporated off in vacuo and the reddish oil was heated thoroughly to constant weight at 50° C. under a high vacuum.

Yield: 25.9 g (91.2% of th.)

EXAMPLE 10

Synthesis of copolymer Copo 1

3.75 g of RM 1, as described in Example 1, were dissolved in 50 ml of toluene, and 11.25 g (0.113 mol) of methyl methacrylate were added. The solution was degassed, and heated at 95° C. under a nitrogen atmosphere for 16 hours. The reaction mixture was added dropwise to 600 ml of methanol and 300 ml of water. The product which had precipitated was separated off by filtration, dissolved again in THF, precipitated in water, separated off and dried. A slightly yellow, flocked powder was obtained.

Yield: 7.6 g (51% of th.) Molecular weight (GPC, THF as the eluent): Mn=53300, Mw=116200 g/mol

EXAMPLE 11

Synthesis of copolymer Copo 2

1.0 g of RM2, as described in Example 2, were dissolved in 50 ml of toluene, and 5.0 g (0.05 mol) of methyl methacrylate were added. The solution was degassed, and heated at 95° C. under a nitrogen atmosphere for 16 hours. The reaction mixture was added dropwise to 400 ml of methanol and 200 ml of water. The product which had precipitated was separated off by filtration, dissolved again in THF, precipitated in water, separated off and dried. A slightly yellow, flocked powder was obtained.

Yield: 2.23 g (37% of th.) Molecular weight (GPC, THF as the eluent): Mn=73500, Mw=204000 g/mol

EXAMPLE 12

Synthesis of copolymer Copo 3

2.5 g of RM2, as described in Example 2, were dissolved in 50 ml of toluene, and 12.5 g (0.125 mol) of methyl methacrylate were added. The solution was degassed, and heated at 95° C. under a nitrogen atmosphere for 16 hours. The reaction mixture was added dropwise to 600 ml of methanol and 300 ml of water. The product which had precipitated was separated off by filtration, dissolved again in THF, precipitated in water, separated off and dried. A yellow, fine powder was obtained.

Yield: 7.8 g (52% of th.) Molecular weight (GPC, THF as the eluent): Mn=26100, Mw=41600 g/mol

EXAMPLE 13

Synthesis of copolymer Copo 4

2.5 g of RM3, as described in Example 3, were dissolved in 50 ml of toluene, and 12.5 g (0.125 mol) of methyl methacrylate were added. The solution was degassed, and heated at 95° C. under a nitrogen atmosphere for 16 hours. The reaction mixture was added dropwise to 400 ml of methanol and 200 ml of water. The product which had precipitated was separated off by filtration, dissolved again in THF, precipitated in water, separated off and dried. A yellow, fine powder was obtained.

Yield: 8.5 g (57% of th.) Molecular weight (GPC, THF as the eluent): Mn=58000, Mw=92800 g/mol

EXAMPLE 14

Synthesis of copolymer Copo 5

0.1 g of RM1, as described in Example 1, were dissolved in 3.5 ml of toluene, and 0.5 g (0.005 mol) of methyl methacrylate was added. The solution was degassed. The reaction mixture was irradiated with an Xe-Hg high pressure lamp (lamp output=200 W, output to the sample=100 W/cm²) in a quartz cell at a distance of 40 cm from the radiation source at room temperature for 16 hours, under nitrogen and while cooling. The reaction mixture was added dropwise to 40 ml of methanol, the precipitate was removed in vacuo and the residue was dried. A yellow, highly viscous product was obtained.

Yield: 0.2 g (30% of th.) Molecular weight (GPC, THF as the eluent): Mn=7300, Mw=14200 g/mol

EXAMPLE 15

Synthesis of copolymer Copo 6

3 g of RM6, as described in Example 6, were dissolved in 50 ml of toluene, and 12.5 g (0.125 mol) of methyl methacrylate were added. The solution was degassed, and heated at 95° C. under a nitrogen atmosphere for 16 hours. The reaction mixture was added dropwise to 400 ml of methanol and 200 ml of water. The product which had precipitated was separated off by filtration, dissolved again in THF, precipitated in water, separated off and dried. A yellow, fine powder was obtained.

Yield: 7.8 g (50.3% of th.) Molecular weight (GPC, THF as the eluent): Mn=46000, Mw=88000 g/mol

EXAMPLE 16

Synthesis of copolymer Copo 7

5 g of RM1, as described in Example 1, and 15 g (0.21 mol) of acrylic acid were dissolved in 50 ml of 1,4-dioxane. The reaction mixture was degassed thoroughly, and stirred at 80° C. for 23 hours. The reaction solution was precipitated in 400 ml of toluene and the product which had precipitated was removed by filtration, dissolved again in 1,4-dioxane and precipitated a second time in 400 ml of toluene. The yellow, brittle product isolated was dried to constant weight under a high vacuum.

Yield: 13.9 g (69.5% of th.)

EXAMPLE 17

Synthesis of copolymer Copo 8

1.5 g of RM7, as described in Example 7, and 4.5 g (0.045 mol) of methyl methacrylate were taken up in 10 ml of toluene. The mixture was degassed thoroughly, and then stirred at 95° C. for 7 hours. Thereafter, the reaction mixture was filtered and the pale yellow, granular residue on the filter was washed with several small portions of tetrahydrofuran. The powder was dried to constant weight under a high vacuum.

Yield: 2.0 g (33.3% of th.)

EXAMPLE 18

Synthesis of copolymer Copo 9

5 g of RM5 and 15 g (0.15 mol) of methyl methacrylate were dissolved in 20 ml of toluene. The reaction mixture was degassed thoroughly, and stirred at 95° C. for 7 hours. The reaction solution was added dropwise to 300 ml of methanol, and the precipitate was filtered off, dissolved again in toluene and precipitated a second time in 300 ml of methanol. The pale yellow product was dried to constant weight under a high vacuum.

Yield: 7.5 g (37.5% of th.)

EXAMPLE 19

Preparation of a blend in a melting press 9 g of polybutadiene (Buna CB 10 from Hüls) were mixed with 1 g of RM1, as described in Example 1, in a conventional laboratory kneader. For additional crosslinking, 72 mg (0.8% by weight of the total system) of dicumyl peroxide were mixed. The mixture was kneaded at 50° C. for 10 minutes. The mixture was then vulcanized in a mold at 150° C. over a period of 60 minutes. The crosslinked, silicone-modified rubber showed better mixing with the silicone component due to chemical bonding via the thermally unstable triazene function than a comparison product comprising polybutadiene and a non-modified silicone oil.

EXAMPLE 20

Crosslinking of an acrylate system 0.2 g of RM5, as described in Example 5, were mixed with 5 g (0.5 mol of acrylate function per kilogram, viscosity 500 mPas) of a polydimethylsiloxane functionalized with acrylate groups, and the mixture was heated at 80° C. for 1 hour. An orange-yellow, completely crosslinked product which is insoluble in organic solvents was obtained.

Yield: 5.2 g (100% of th.)

EXAMPLE 21

Crosslinking by heat 1 g of RM5, as described in Example 5, was applied as a film to a glass plate and then stored at 130° C. in a heating cabinet for 1 hour. A reddish, completely crosslinked and insoluble film was obtained.

Yield: 0.95 g (95% of th.)

EXAMPLE 22

Crosslinking by light 1 g of RM3, as described in Example 3, was applied as a film to a glass plate and then exposed to LFV light (UVA=56 mW/cm$^2$, UVB=12 mW/cm$^2$) for 1 hour. A red, completely crosslinked product which is insoluble in organic solvents was obtained.

Yield: 0.98 g (98% of th.)

What is claimed is:

1. An organosilicon compound having at least one Si—C-bonded organic radical which contains at least one triazene group wherein the triazene group is bonded to the organosilicon compound by at least one divalent organic radical.

2. An organosilicon compound as claimed in claim 1, containing at least one triazene group of the formula

in which
X is a radical of the formula

a radical $R^2$ or half a divalent radical $R^3$, with the proviso that at least one X per unit of formula 1 is a radical of formula 2, and optionally units of the formula

wherein, in the above formulae 1 to 3,

R is a divalent Si—C-bonded $C_1$- to $C_{18}$-hydrocarbon radical, $R^1$ and $R^2$ are a hydrogen atom, a hydroxyl group, a halogen group or a monovalent $C_1$- to $C_{18}$-hydrocarbon or hydrocarbonoxy radical, $R^3$ is a divalent $C_1$- to $C_{18}$-hydrocarbon radical and m and n represent 0, 1, 2 or 3.

3. A process for the preparation of an organosilicon compound as claimed in claim 1, in which a diazonium salt is reacted with a primary or secondary amine, wherein at least one of the radicals on the diazonium salt or amine having an Si—C-bonded organosilicon radical.

4. A process for the preparation of an organosilicon compound as claimed in claim 3, in which (A) a triazene compound containing halogen atoms, carboxylic acid anhydride or epoxide groups or —COCl or —NCO groups is reacted with an organosilicon compound having —OH, —NHR$^1$, —COOH or —SH groups, or (B) a triazene compound containing —OH, —NHR$^1$, —COOH or —SH groups is reacted with an organosilicon compound having halogen atoms, carboxylic acid anhydride or epoxide groups or —COCl or —NCO groups, wherein R$^1$ is a hydrogen atom, a hydroxyl group, a halogen group or a monovalent $C_1$ to $C_{18}$-hydrocarbon or hydrocarbonoxy radical.

5. A process for the preparation of an organosilicon compound as claimed in claim 1, wherein a triazene compound containing radicals which have olefinic double bonds or acetylenic triple bonds is reacted with an organosilicon compound having Si—H groups in the presence of platinum, rhodium or compounds thereof.

6. A process for the preparation of a homopolymer, graft copolymer or block copolymer, in which an organosilicon compound as claimed in claim 1 is reacted with an organic compound by free radical polymerization.

7. A homopolymer, graft copolymer and/or block copolymer obtainable by the process as claimed in claim 6.

8. A process for crosslinking an organosilicon compound and an organic compound capable of being polymerized by free radical polymerization, wherein the organic compound is mixed with an organosilicon compound as claimed in claim 1 and the mixture is heated or irradiated with UV light.

9. A process for the preparation of an organosilicon compound as claimed in claim 1, wherein a silane containing groups capable of undergoing condensation is hydrolyzed, condensed or equilibrated with a silane or siloxane.

10. An organosilicon compound as claimed in claim 2 wherein R, $R^1$, $R^2$ and $R^3$ are substituted by hydroxyl, $C_1$- to $C_6$-alkoxy, mercapto, epoxide or cyano groups or halogen atoms.

11. An organosilicon compound as claimed in claim 2, wherein R, $R^1$, $R^2$ and $R^3$ contain ether, thioether, amine, ester, carbonyl, urethane, urea, sulfonyl or amide bonds.

12. A process as claimed in claim 4, wherein $R^1$ is substituted by hydroxyl, $C_1$- to $C_6$-alkoxy, mercapto, epoxide or cyano groups or halogen atoms.

13. A process as claimed in claim 4, wherein $R^1$ contains ether, thioether, amine, ester, carbonyl, urethane, urea, sulfonyl or amide bonds.

* * * * *